United States Patent [19]

Scheyer

[11] Patent Number: 5,810,711
[45] Date of Patent: Sep. 22, 1998

[54] DEVICE FOR USE IN ENDOSCOPY AND LAPAROSCOPY

[75] Inventor: Mathias Scheyer, Feldkirch, Austria

[73] Assignee: Hafslund Nycomed Pharma Aktiengesellschaft, Linz, Austria

[21] Appl. No.: 643,952

[22] Filed: May 7, 1996

[30] Foreign Application Priority Data

May 16, 1995 [AT] Austria ...................................... 830/95

[51] Int. Cl.$^6$ .................................................. A61B 1/018
[52] U.S. Cl. ................................................ 600/104; 606/1
[58] Field of Search .................................. 600/101, 104, 600/193, 201, 204, 206, 210, 211, 215, 216; 604/19, 57, 61, 14, 15, 16, 21; 606/1

[56] References Cited

U.S. PATENT DOCUMENTS

| | | | |
|---|---|---|---|
| 2,028,635 | 1/1936 | Wappler | 600/104 X |
| 2,269,963 | 1/1942 | Wappler | 604/61 |
| 3,856,016 | 12/1974 | Davis | 600/104 X |
| 4,027,510 | 6/1977 | Hiltebrandt | 600/104 X |
| 4,122,556 | 10/1978 | Poler | 604/295 X |
| 5,176,692 | 1/1993 | Wilk et al. | 606/1 X |
| 5,263,969 | 11/1993 | Phillips | 606/1 X |
| 5,304,187 | 4/1994 | Green et al. | 604/15 X |
| 5,307,805 | 5/1994 | Byrne | 600/227 X |
| 5,381,788 | 1/1995 | Matula et al. | 600/215 X |

FOREIGN PATENT DOCUMENTS 0 543 499  5/1993  European Pat. Off. .

*Primary Examiner*—Jeffrey A. Smith
*Attorney, Agent, or Firm*—Wenderoth, Lind & Ponack, L.L.P.

[57] ABSTRACT

A device for endoscopic or laparoscopic application of surgical material has a hand grip 1 and a shaft 2 surrounded by a movable tube 3, at a end of which shaft 2 there is a closure for an appliance for securing the wound-healing or wound-sealing material or a surgical instrument. The closure has two branches 6 which are of different lengths and are connected in a U-shape, a notch 7 being provided on the longer branch. An a raised portion 8 is provided on the appliance for securing the wound-healing or wound-sealing material or on the surgical material, which raised portion 8 can be inserted with an exact fit into the notch in the longer branch.

21 Claims, 4 Drawing Sheets

DEVICE FOR USE IN ENDOSCOPY AND LAPAROSCOPY

BACKGROUND OF THE INVENTION

The invention relates to a device for endoscopic or laparoscopic application of surgical material, in particular wound-sealing or wound-healing material.

Endoscopic or laparoscopic operations require the use of special surgical instruments which are adapted for use in trocars or laparoscopes. A particular problem in this context is the accurate and safe positioning and fixing of surgical instruments and/or aids at the desired site in the body.

EP-A-0,543,499 discloses an appliance for introducing and positioning an antiadhesion layer, where the antiadhesion material is fixed at the desired site with the aid of a liquid, for example a physiological saline solution, issuing from a nozzle. This appliance has the disadvantage that the material to be applied, before being introduced into the body, can be secured on the applicator only to an inadequate extent and therefore demands great dexterity during handling.

SUMMARY OF THE INVENTION

The object of the present invention is therefore to provide a device for use in endoscopic or laparoscopic operations which guarantees, on the one hand, the reliable securing of surgical instruments or aids, in particular wound-sealing or wound-healing material, and, on the other hand, the reliable maneuverability and accurate positioning of the instrument or aid at the desired site.

The subject of the invention is therefore a device for endoscopic or laparoscopic application of surgical material, having a hand grip and, a shaft 2 surrounded by a movable tube 3. At the end of the shaft 2 there is a closure for an appliance for securing the wound-healing or wound-sealing material or a surgical instrument, this closure having two branches 6 which are of different lengths and are connected in a U-shape. A notch 7 is provided on the longer branch, and the appliance for securing the wound-healing or wound-sealing material or the surgical aid is provided with a raised portion 8 which can be inserted with an exact fit into the notch in the longer branch.

In this way, a reliable fixing of the instrument or material to be introduced into the body is guaranteed.

The expression surgical material is used in this application for surgical instruments, aids and wound-healing or wound-sealing material.

DETAILED DESCRIPTION OF THE PREFERRED EMBODIMENTS

Figure 1:
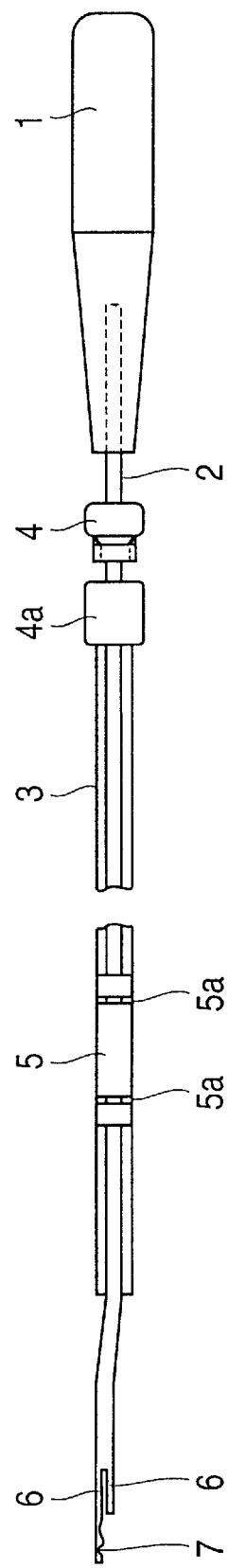
FIG. 1 shows a device according to the invention.
Figure 2:
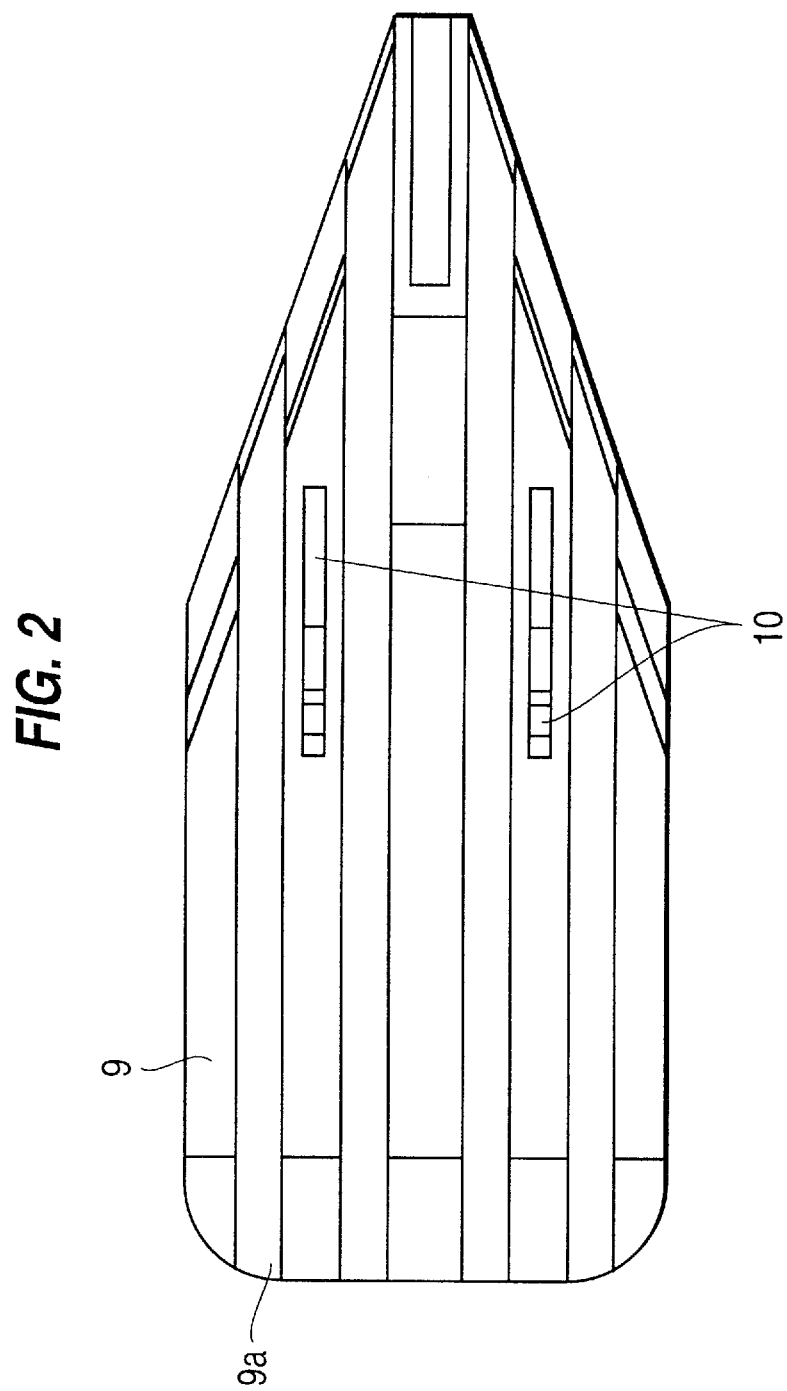
FIG. 2 shows a plan view of an appliance for securing a wound-healing or wound-sealing material.
Figure 3:
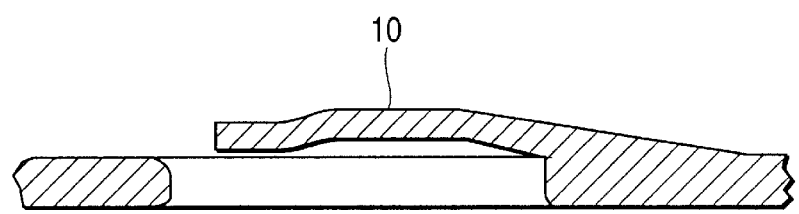
FIG. 3 shows a partial section through the appliance shown in FIG. 2.
Figure 4:
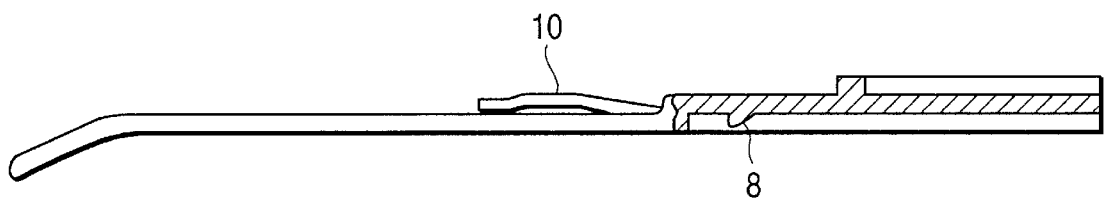
FIG. 4 shows a vertical section of the appliance for securing the wound-healing or wound-sealing material.
Figure 5:
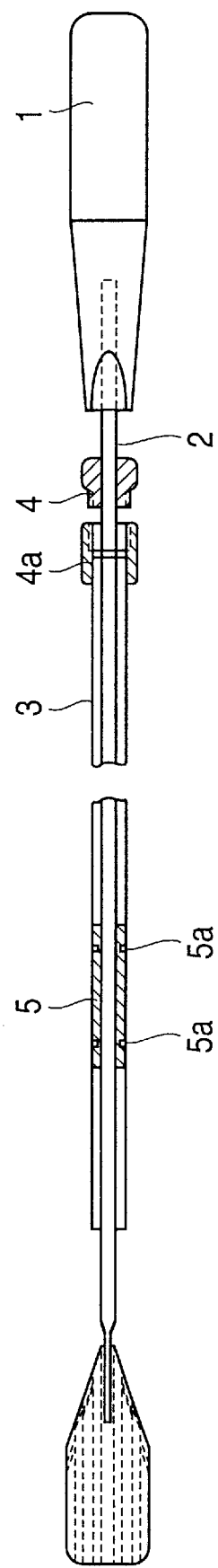
FIG. 5 shows the device together with the appliance for securing the wound-healing or wound-sealing material.

In the drawings, 1 denotes a grip of a device, 2 a shaft fixed thereon, 3 a movable tube, 4 a closure screw, 4a a sleeve, 5 a bearing and 5a a sealing ring, 6 a two branches of different lengths which are connected in a U-shape, 7 a notch in the longer branch, 8 a raised portion on an appliance for securing wound-healing or wound-sealing material, 9 and 9a a movable lamellae, and 10 flaps for securing the wound-healing or wound-sealing material.

Before being introduced into the trocar by moving the tube 3, the instrument secured on the shaft 2, or the appliance for securing the wound-healing or wound-sealing material, is concealed in the tube 3 and is released, only when it has reached the desired site in the body, by pulling the tube 3 back. In this way, the instrument or material to be introduced into the body does not come into direct contact with the trocar, as a result of which soiling, by blood for example, is avoided, and the possibility of the material being damaged during introduction is ruled out. In addition, there is a uniform and rapid sealing effect, independent of the material introduced, with a defined eccentric bearing between the active region and the handling region.

The shaft 2 and tube 3 can be made of any suitable material, for example metal, such as stainless and acid-resistant steel, or plastics, such as glass-fiber-reinforced PSU. Another point to note is that these materials can be sterilized and resterilized by means of the traditionally employed sterilization methods. An advantageous design is one in which these parts are as light as possible, but stable.

The grip 1 is preferably made of aluminum or nonslip plastic.

The tube 3 is arranged on the shaft so that it can be moved in the axial direction, preferably with the aid of the sleeve 4a. The closure screw 4 mounted on the shaft 2 prevents the tube from being pulled back too far. The bearing 5 with the sealing ring 5a is preferably provided for accurately guiding the tube, in which case the bearing 5 can be made of stainless and acid-resistant steel, and the sealing ring 5a can be made of silicone or other sterilizable plastics.

The shaft 2 has a kink preferably in the vicinity of the branches 6 connected in a U-shape. A defined, eccentric positioning of the secured surgical material, or of the appliance for securing it, is achieved in this way. That is, the kink in the shaft 2 is provided so as to form an eccentric bearing, whereby the active region including the branches 6 is on one side of the eccentric bearing and the handling region, including the handle 1, is on the other side of the eccentric bearing.

A further subject of the invention is the appliance for securing a wound-healing or wound-sealing material, which has of movable lamellae 9 and 9a and which is provided on an inner side with flaps 10 for receiving the wound-sealing or wound-healing material.

This appliance is preferably in the form of a rounded and beveled plate and can be made of sterilizable plastic, such as polypropylene or the like, and is preferably intended for one-off use. The lamellae 9 and 9a must in this case be sufficiently stable, and yet flexible, in order to be able to accurately define the contact pressure at the desired site and at the same time to fix, by slight withdrawal, the wound-healing or wound-sealing material at this site. The rounded and beveled plate thus has the flexible lamellae extending in a longitudinal direction of the plate. As can be seen from the drawing figures, the plate has a connection end and a free end opposite to the connection end. The flaps extend toward the free end of the plate. The connection end includes the raised portion 8 as a connecting arrangement.

The appliance is secured in the notch 7 of the shaft 2 via the raised portion 8 provided on the rear of the appliance. The movable tube 3 is then pulled over the appliance, whereupon the movable lamellae 9, 9a close in a cone shape and enclose the wound-sealing or wound-healing material. By having the flexible lamellae extend in the longitudinal direction, the plate is capable of being closed together in the cone shape by bending the plate in a direction that is generally perpendicular to the longitudinal direction.

The device is then introduced into the trocar, and the lamellae are unfolded at the desired site by pulling back the tube 3. The wound-healing or wound-sealing material can then be released from its securement in the flaps 10, by slight pressing and pulling, and fixed at the desired site.

What I claim is:

1. A device, comprising:
   a hand grip;
   a shaft connected with said hand grip, said shaft having a closure at one end of said shaft that is adapted to be connected with an appliance used to secure a surgical material, said closure comprising two branches of different lengths and connected in a U-shape, wherein a longer one of said two branches comprises a notch that is adapted to be engaged with a raised portion on the appliance or on the surgical material; and
   a movable tube surrounding said shaft.

2. The device of claim 1, wherein said shaft has a kink at said one end thereof adjacent to said two branches of said closure, whereby an active region is defined at said one end of said shaft, a handling region is defined at the other end of said shaft, and said kink forms an eccentric bearing between said active region and said handling region.

3. The device of claim 1, wherein said device consists of said hand grip, said shaft, and said movable tube.

4. An apparatus for endoscopic or laparoscopic application of surgical material, comprising:
   an appliance for securing a surgical material, said appliance having a raised portion; and
   a device comprising:
      a hand grip;
      a shaft connected with said hand grip, said shaft having a closure at one end of said shaft that is adapted to be connected with said appliance, said closure comprising two branches of different lengths and connected in a U-shape, wherein a longer one of said two branches comprises a notch that is engaged with said raised portion on said appliance such that said raised portion is inserted into said notch with an exact fit; and
      a movable tube surrounding said shaft.

5. The apparatus of claim 4, wherein said shaft has a kink at said one end thereof adjacent to said two branches of said closure, whereby an active region is defined at said one end of said shaft, a handling region is defined at the other end of said shaft, and said kink forms an eccentric bearing between said active region and said handling region.

6. The apparatus of claim 5, wherein said appliance comprises a rounded and beveled plate.

7. The apparatus of claim 5, wherein said appliance comprises movable lamellae and flaps on an inner side of said appliance for securing the surgical material.

8. The apparatus of claim 7, wherein said appliance comprises a rounded and beveled plate.

9. The apparatus of claim 8, wherein said flaps are cantilevered members that are raised relative to said plate.

10. The apparatus of claim 8, wherein said appliance consists of said rounded and beveled plate.

11. The apparatus of claim 4, wherein said appliance comprises a rounded and beveled plate.

12. The apparatus of claim 4, wherein said movable tube is movable between a position in which said end of said shaft and said appliance are covered by said movable tube, and a position in which said end of said shaft and said appliance is uncovered.

13. The apparatus of claim 12, wherein said movable tube has a sleeve at a proximal end thereof.

14. The apparatus of claim 13, wherein said shaft has a closure screw thereon between said sleeve and said handle for stopping movement of said movable tube toward said handle.

15. The apparatus of claim 4, wherein said apparatus consists of said appliance, said hand grip, said shaft and said movable tube.

16. The apparatus of claim 15, wherein said shaft has a kink at said one end thereof adjacent to said two branches of said closure, whereby an active region is defined at said one end of said shaft, a handling region is defined at the other end of said shaft, and said kink forms an eccentric bearing between said active region and said handling region.

17. The apparatus of claim 4, wherein said device consists of said hand grip, said shaft and said movable tube.

18. An appliance for securing surgical material, said appliance comprising:
    a rounded and beveled plate comprising flexible lamellae extending in a longitudinal direction such that said plate is capable of being closed together by bending said plate in a direction that is generally perpendicular to the longitudinal direction for the purpose of enclosing the surgical material therein, said plate having a connection end and a free end at opposite ends thereof in the longitudinal direction;
    flaps comprising members on the inner side of said plate and extending toward the free end of said plate for securing the surgical material to the inner side of said plate; and
    a connecting arrangement at the connection end of said plate for connecting said plate to a handling device.

19. The appliance of claim 18, wherein said flaps are cantilevered members that are raised relative to said plate.

20. The appliance of claim 18, wherein said appliance consists of said rounded and beveled plate, said flaps and said connecting arrangement.

21. The appliance of claim 18, wherein said flaps extend from said plate at a position closer to the connection end of said plate than the free end in the longitudinal direction of said plate.

* * * * *